(12) United States Patent
Izawa et al.

(10) Patent No.: US 9,126,963 B2
(45) Date of Patent: *Sep. 8, 2015

(54) METHOD FOR PRODUCING TETRAHYDROFURAN

(71) Applicant: MITSUBISHI CHEMICAL CORPORATION, Chiyoda-ku (JP)

(72) Inventors: Yusuke Izawa, Mie (JP); Masaru Utsunomiya, Tokyo (JP); Eiji Hattori, Mie (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/147,894

(22) Filed: Jan. 6, 2014

(65) Prior Publication Data

US 2014/0121390 A1    May 1, 2014

Related U.S. Application Data

(63) Continuation of application No. PCT/JP2012/067013, filed on Jul. 3, 2012.

(30) Foreign Application Priority Data

Jul. 4, 2011    (JP) .................................. 2011-148329

(51) Int. Cl.
    *C07D 307/02*        (2006.01)
    *C07D 307/08*        (2006.01)

(52) U.S. Cl.
    CPC ..................................... *C07D 307/08* (2013.01)

(58) Field of Classification Search
    CPC .............................. C07D 307/08; C08G 65/20
    USPC .................................. 549/509; 502/217, 349
    See application file for complete search history.

(56) References Cited

U.S. PATENT DOCUMENTS

| | | | |
|---|---|---|---|
| 5,319,111 A | 6/1994 | Zimmermann et al. |
| 6,137,016 A | 10/2000 | Wood et al. |
| 6,316,640 B1 | 11/2001 | Fischer et al. |
| 7,098,349 B2 | 8/2006 | Pinkos et al. |
| 2003/0100777 A1 | 5/2003 | Wood et al. |
| 2006/0122365 A1 | 6/2006 | Pinkos et al. |
| 2010/0101931 A1 | 4/2010 | Pinkos et al. |

FOREIGN PATENT DOCUMENTS

| | | |
|---|---|---|
| JP | 7-53538 | 2/1995 |
| JP | 08-217707 A | 8/1996 |
| JP | 10-077277 | 3/1998 |
| JP | 10-077277 A | 3/1998 |
| JP | 2006-503050 | 1/2006 |
| JP | 2010-518174 | 5/2010 |
| WO | 01-44148 | 6/2001 |
| WO | 2004/026853 | 4/2004 |
| WO | 2008/098621 | 8/2008 |

OTHER PUBLICATIONS

International Search Report issued Aug. 14, 2012 in PCT/JP2012/067013 filed Jul. 3, 2012.
U.S. Appl. No. 14/147,932, filed Jan. 6, 2014, Izawa, et al.
Chinese Office Action dated Dec. 18, 2014, in Chinese Patent Application No. 201280032732.8, with English translation (11 pages).

*Primary Examiner* — Andrew D Kosar
*Assistant Examiner* — Raymond Covington
(74) *Attorney, Agent, or Firm* — Oblon, McClelland, Maier & Neustadt, L.L.P.

(57) ABSTRACT

The present invention relates to a method for producing tetrahydrofuran comprising: feeding raw material 1,4-butanediol containing gamma butyrolactone to a reaction tank, and performing a dehydration cyclization reaction in the presence of a homogeneous acid catalyst having a pKa of 4 or less and being dissolvable in 1,4-butanediol to produce tetrahydrofuran, wherein a gas containing tetrahydrofuran, gamma butyrolactone and water in the reaction tank is introduced into a heat exchanger and when obtaining a condensate from the outlet of the heat exchanger, the ratio of the concentration of gamma butyrolactone in the condensate based on the concentration of gamma butyrolactone in the raw material 1,4-butanediol is from 20 to 100%.

5 Claims, No Drawings

METHOD FOR PRODUCING TETRAHYDROFURAN

TECHNICAL FIELD

The present invention relates to a method for producing tetrahydrofuran. More specifically, the present invention relates to a method for producing tetrahydrofuran from 1,4-butanediol under heating condition by using an acid catalyst.

BACKGROUND ART

Tetrahydrofuran (hereinafter, sometimes simply referred to as "THF") is used as a solvent for various organic compounds and is known to be a compound useful also as a raw material of a polyether polyol such as polytetramethylene ether glycol.

As the industrial production method of a cyclic ether such as tetrahydrofuran, a variety of production methods have been conventionally known, but among others, the cyclic ether is produced in many cases by dehydration cyclization of a dihydroxy compound such as 1,4-butanediol (hereinafter, sometimes simply referred to as "1,4BG"). As the catalyst for the dehydration cyclization reaction of a dihydroxy compound, an acid catalyst is known to be effective in view of high conversion ratio and selectivity, and, for example, Patent Document 1 describes a method where an alkanediol such as 1,4-butanediol is dehydrogenated and dehydrated in the presence of a cobalt-containing catalyst, an organic sulfonic acid and a high-boiling-point amine to produce an α,β-cyclic unsaturated ether such as dihydrofuran. Also, Patent Document 2 describes a method for continuously producing THF by a reaction of a 2-(4-hydroxybutoxy)tetrahydrofuran-containing 1,4BG reaction mixture on a heteropolyacid catalyst.

The raw material 1,4-butanediol used for THF production can be obtained by conventionally known various production methods of 1,4BG, and with respect to the product 1,4BG obtained, a byproduct occurring in the production process may be slightly mixed as an impurity into the product 1,4BG. The kind or amount of the impurity varies depending on the production method of 1,4BG, and Patent Document 2 discloses that when 1,4BG containing 2-(4-hydroxybutoxy)tetrahydrofuran which is one of impurities is used as a raw material to produce THF, a high-boiling-point component occurs as a byproduct in the reactor for THF production. Also, Patent Document 3 discloses that a water-containing crude product obtained by hydrogenating 1,4-butynediol contains gamma butyrolactone other than 1,4BG, and it is stated that the gamma butyrolactone is separated from the crude product by using a distillation column.

BACKGROUND ART DOCUMENT

Patent Document

Patent Document 1: JP-A-10-77277 (the term "JP-A" as used herein means an "unexamined published Japanese patent application")
Patent Document 2: JP-T-2006-503050 (the term "JP-T" as used herein means a published Japanese translation of a PCT patent application)
Patent Document 3: JP-T-2010-518174

SUMMARY OF INVENTION

Problem that Invention is to Solve

According to the method described in Patent Document 3, 1,4BG from which most of gamma butyrolactone is separated and removed can be obtained, but this method has been found to have a problem that the 1,4-butanediol is in the state of allowing a slight amount of gamma butyrolactone incapable of being sufficiently separated to exist therein and when THF is obtained as a product by performing a dehydration cyclization reaction using this 1,4BG as a raw material, a high-boiling-point byproduct derived from gamma butyrolactone accumulates in the reactor for THF production and inhibits the operation.

The present invention has been made by taking into account the above-described problem, and an object of the present invention is to provide an industrially advantageous production method of THF, ensuring that in the method for producing THF from 1,4-butanediol by using an acid catalyst, reduction in the reaction selectivity due to an impurity contained in 1,4-butanediol and production of a high-boiling byproduct are suppressed and high productivity is stably obtained.

Means for Solving Problem

As a result of intensive studies to attain the above-described object, the present inventors have found that when at the time of producing tetrahydrofuran by performing a dehydration cyclization reaction of raw material 1,4-butanediol containing gamma butyrolactone in the presence of an acid catalyst with a pKa of 4 or less, a gas containing tetrahydrofuran, water and gamma butyrolactone is withdrawn from a reaction tank having a gas phase and a liquid phase under heating and at the time of introducing the gas into a heat exchanger and obtaining a condensate from the outlet of the heat exchanger, the reaction is controlled to make the amount of gamma butyrolactone contained in the condensate to stay at a certain fixed amount based on the gamma butyrolactone in the raw material 1,4-butanediol, a high-boiling byproduct derived from gamma butyrolactone can be prevented from accumulating in the reaction tank and reduction in the reaction selectivity can be suppressed.

The present invention has been accomplished based on this finding and the gist of the present invention resides in the following (1) to (5).

(1) A method for producing tetrahydrofuran, comprising feeding raw material 1,4-butanediol containing gamma butyrolactone to a reaction tank, and performing a dehydration cyclization reaction in the presence of a homogeneous acid catalyst having a pKa of 4 or less and being dissolvable in 1,4-butanediol to produce tetrahydrofuran, wherein a gas containing tetrahydrofuran, gamma butyrolactone and water in the reaction tank is introduced into a heat exchanger and when obtaining a condensate from the outlet of the heat exchanger, the ratio of the concentration of gamma butyrolactone in the condensate based on the concentration of gamma butyrolactone in the raw material 1,4-butanediol is from 20 to 100%.

(2) The production method of tetrahydrofuran described in the above (1), wherein the temperature of a liquid phase part in the reaction tank is from 80 to 250° C.

(3) The production method of tetrahydrofuran described in the above (1) or (2), wherein the concentration of the homogeneous acid catalyst in the reaction tank is from 0.01 to 20.0 wt %.

(4) The production method of tetrahydrofuran described in any one of the above (1) to (3), wherein the homogeneous acid catalyst is mixed with and dissolved in the raw material 1,4-butanediol and then fed to the reaction tank.

(5) The production method of tetrahydrofuran described in any one of the above (1) to (4), wherein the concentration of gamma butyrolactone in the reaction tank is kept at 20 ppm by weight to 1 wt %.

Advantageous Effects of Invention

According to the present invention, tetrahydrofuran can be efficiently produced from 1,4-butanediol containing gamma butyrolactone as an impurity while reducing the production of a high-boiling byproduct and avoiding reduction in the reaction selectivity.

MODE FOR CARRYING OUT INVENTION

A best mode for carrying out the present invention (hereinafter, the embodiment of the invention) is described in detail below. Incidentally, the present invention is not limited to the following embodiment but can be carried out by making various modifications therein within the gist of the present invention. Here, "wt %" and "ppm by weight" have the same meanings as "mass %" and "ppm by mass", respectively.

The raw material 1,4-butanediol for use in the present invention can be obtained by a known method. For example, 1,4BG obtained by performing hydrogenation and hydrolysis of 1,4-diacetoxy-2-butene that is obtained by diacetoxylation of butadiene may be used.

Alternatively, for example, 1,4BG obtained by hydrogenation of maleic anhydride, 1,4BG derived from acetylene by the Reppe process, 1,4BG obtained through oxidation of propylene, 1,4BG obtained by hydrogenating succinic acid that is obtained by a fermentation process, and 1,4BG produced directly from sugar by a fermentation process can be used.

The raw material 1,4BG for use in the present invention contains gamma butyrolactone, and the concentration of gamma butyrolactone in the raw material 1,4BG is 20 ppm by weight or more, preferably 50 ppm by weight or more, more preferably 100 ppm by weight or more. As this amount becomes larger, the load of separation from gamma butyrolactone in the production process of 1,4BG can likely be reduced. On the other hand, the concentration of gamma butyrolactone in the raw material 1,4BG is preferably 10 wt % or less, more preferably 5 wt % or less, still more preferably 2 wt % or less. As this value becomes smaller, the effect of gamma butyrolactone during THF production can tend to be reduced. Incidentally, the raw material 1,4BG where the concentration of gamma butyrolactone is in the range above can be obtained by a production method of 1,4BG involving occurrence of gamma butyrolactone as a byproduct, such as hydrogenation of maleic anhydride, hydrogenation of succinic acid, and Reppe process. Furthermore, in these production methods, gamma butyrolactone is distilled and removed from 1,4BG, and the amount of gamma butyrolactone contained in 1,4BG is determined by the degree of this distillation separation. Also, gamma butyrolactone may be mixed with 1,4BG to achieve the concentration in the range above.

The reaction tank as used in the present invention has the same meaning and content as a reactor, a reaction vessel, a reaction kettle, a reaction column or the like and is not particularly limited as long as it is a vessel capable of performing a dehydration cyclization reaction. In the case where the dehydration cyclization reaction reaches chemical equilibrium, a reaction proceeds by removing the reaction product water from the reaction tank and therefore, a structure having, in the inside of the reaction tank, a reaction part for performing a reaction by allowing the raw material, catalyst or product to exist in liquid phase, a liquid phase part composed of water mainly produced by the reaction and a gas phase part composed of a low volatile product, is preferably constructed. The liquid phase part of the reaction tank is continuously or intermittently withdrawn out of the reaction tank along with the progress of reaction, whereby the reaction proceeds. In the case of a reaction where, as in the present invention, THF is produced by a dehydration cyclization reaction of raw material 1,4BG in the presence of a homogeneous acid catalyst having a pKa value of 4 or less, the homogenous acid catalyst having pKa value of 4 or less is caused to exist in the reaction part, the raw material 1,4BG is fed to the reaction part, the gas phase part contains THF volatilized, gamma butyrolactone contained in the raw material 1,4BG, and a part of water vapor, which are produced by the reaction, and the liquid phase part of the reaction part contains the remaining water and a byproduct.

At this time, the reaction is performed while heating the reaction tank, and the heating system of the reaction tank may be a system where a heat medium such as steam is brought into contact with an external jacket to perform heating or may be a system where a heat transfer device such as coil is provided inside the reaction tank and performs heating. The material for such an inside of the reaction tank is not particularly limited and a known material may be used, but from the standpoint that corrosion can be reduced, SUS304, SUS316, SUS316L, Hastelloy, titanium, glass and the like are preferably used.

In the reaction tank of the present invention, usually, a stirrer for uniformly and efficiently perform the dehydration cyclization reaction may be provided. The stirrer is not particularly limited. The stirrer usually consists of an electric motor, a shaft and a stirring blade, and the stirring blade is also not limited in its shape.

In the present invention, a gas containing THF, gamma butyrolactone and water, which are produced in the reaction part inside the reaction tank, is present in the gas phase part. This gas is introduced into a heat exchanger and condensed/liquefied in the heat exchanger, whereby a condensate of tetrahydrofuran containing gamma butyrolactone can be obtained The heat exchanger above is a device for condensing/liquefying a gas (distillate) occurring in the reaction tank, and the condensation/liquefaction is performed by exchanging heat between the distillate and an external fluid that is a cooling liquid. Incidentally, the gas containing THF, gamma butyrolactone and water may contain product water from a raw material charged in the form of an aqueous solution, a dehydration solvent used for azeotroping with product water, if desired, and the like.

Also, in the present invention, the concentration of gamma butyrolactone in the solution inside the reaction tank is kept at 20 ppm by weight to 1 wt % by controlling the distillate volume of gamma butyrolactone in the condensate above. There is a tendency that as the gamma butyrolactone concentration in the condensate becomes smaller, the recycled amount of raw material 1,4BG increases and as the gamma butyrolactone concentration becomes larger, the amount of a high-boiling product in the reaction tank increases. The method for controlling the distillate volume of gamma butyrolactone in the condensate is not particularly limited as long as the distillate volume can be controlled, but the distillate volume can be controlled by adjusting the heat medium temperature, the reaction temperature, the pressure in the reaction tank, the reflux, the introduction of a gas such as nitrogen, and in the case of a reaction column where the reaction tank has a tray, the number of trays or the parameters such as reflux ratio. The gamma butyrolactone has a higher boiling point than THF and a lower boiling point than raw material 1,4BG and therefore, the reaction tank is preferably controlled to sufficiently distill out the product THF in the form of a gas from the reaction tank and at the same time, retain 1,4BG in the reaction tank.

Incidentally, a distillation column such as packed column and plate column for previously separating high-boiling-point components from the gas containing THF, gamma butyrolactone and water may be provided immediately before introduction into a heat exchanger. The number of plates of the packed column, plate column or the like may be arbitrary but usually, in terms of theoretical plates, is preferably from 1 to 100, more preferably from 3 to 20. As the number of plates is increased, the size of the distillation column for separation becomes too large, and the economic efficiency in view of construction of the facility may be reduced. Also, as the number of plates becomes smaller, THF, gamma butyrolactone and water to be distilled out are difficult to separate from 1,4BG retained in the reactor.

In the present invention, it is also possible that a gas containing produced THF, gamma butyrolactone and water is discharged from the gas phase part of the reaction tank and condensed by a heat exchanger and a condensate is obtained from the outlet of the heat exchanger and partially returned to the gas phase part inside the reaction tank. The composition of the condensed liquid contains THF, gamma butyrolactone and water at arbitrary concentrations, but the THF concentration is preferably from 30 to 95 wt %, more preferably from 50 to 85 wt %. Also, the dehydration cyclization reaction of the present invention produces water stoichiometrically, and the water concentration in the condensate is usually from 1 to 50 wt %, preferably from 5 to 30 wt %, more preferably from 15 to 25 wt %.

In the present invention, the ratio (sometimes referred to as the percentage) of the concentration of gamma butyrolactone in the condensate based on the concentration of gamma butyrolactone in the raw material 1,4-butanediol must be from 20 to 100%. By satisfying this ratio, accumulation of gamma butyrolactone in the reaction tank can be avoided and production of a high-boiling byproduct such as dimer of 1,4BG and gamma butyrolactone can be reduced. The percentage above is preferably from 30 to 95%, more preferably from 40 to 90%. As this percentage becomes larger, production of a high-boiling byproduct tends to be reduced by avoiding accumulation of gamma butyrolactone in the reaction tank. Also, if this percentage is less than 20%, accumulation of gamma butyrolactone in the reaction tank may proceed and production of a high-boiling byproduct may be disadvantageously increased.

As for the technique to control this percentage to the range above, the gamma butyrolactone concentration in the reaction tank is preferably kept at 20 ppm by weight to 1 wt %, as described above, but the percentage may be controlled to the range above by adjusting other reaction conditions.

At the time of returning a part of the condensate obtained from the outlet of the heat exchanger to the gas phase part inside the reaction tank and withdrawing the remaining condensate out of the reaction tank, the ratio between the flow rate of the condensate fed to the gas phase part of the reaction tank and the flow rate of the condensate withdrawn out of the reaction tank (hereinafter, sometimes referred to as "reflux ratio") is usually from 0.001 to 30, preferably from 0.01 to 10.00, more preferably from 0.1 to 3.0. Incidentally, if the reflux ratio is too high, the cost of a heat source for heating is increased to worsen the economic efficiency, whereas if the reflux ratio is too low, the effect of reducing precipitation of a solid in the reaction tank is not obtained and mixing of a high-boiling-point component into the condensate proceeds due to bad separation of the component. The temperature at the introduction of a gas containing THF and water to be introduced into the heat exchanger is preferably from 10 to 200° C., more preferably from 60 to 100° C. An optimal value of the reflux ratio is determined in relation to the reaction temperature, the reaction conditions and the design conditions of a reaction tank, but in general, if the reflux ratio is too high, an enormous consumption of energy is required, whereas if the reflux ratio is too low, distillation of 1,4BG together with gamma butyrolactone is increased.

As the catalyst in the present invention, a homogeneous acid catalyst having a pKa of 4 or less and being dissolvable in 1,4-butanediol (hereinafter, sometimes referred to as "acid catalyst") is used and, among these, an organic sulfonic acid is preferred. Specifically, the organic sulfonic acid is an aromatic sulfonic acid derivative such as para-toluenesulfonic acid, benzenesulfonic acid, ortho-toluenesulfonic acid and meta-toluenesulfonic acid, or a chain hydrocarbon sulfonic acid derivative such as butanesulfonic acid, hexanesulfonic acid, octanesulfonic acid and nonanesulfonic acid. These may be used as a mixture and may contain a functional group other than a sulfonic acid in the carbon skeleton. Above all, a para-toluenesulfonic acid is preferred. In the present invention, a THF-producing reaction by the dehydration cyclization of raw material 1,4BG proceeds in the reaction part inside the reaction tank, and the concentration of the acid catalyst in the reaction tank is from 0.01 to 20 wt %, preferably from 0.05 to 10 wt %, more preferably from 0.2 to 5 wt %. Here, the water concentration of the liquid phase part inside the reaction tank is usually from 0.1 to 5.0 wt %, preferably from 0.2 to 4.0 wt %, more preferably from 0.3 to 3.0 wt %. As this concentration becomes higher, corrosion of the material tends to be accelerated, and as the concentration becomes lower, the amount of a high-boiling-point byproduct is likely to increase.

Incidentally, at the start of reaction, the reaction can also be started by previously causing the acid catalyst to exist in the reaction part of the reaction tank before feeding raw material 1,4BG and starting the reaction, but from the standpoint of suppressing reduction in the reaction yield due to deterioration of the catalyst, it is more effective to successively charge the acid catalyst into the reaction tank. For example, the acid catalyst is preferably mixed with and dissolved in raw material 1,4BG and intermittently or continuously fed to the reaction tank. In this connection, the liquid phase part inside the reaction tank may be intermittently or continuously withdrawn out of the reaction tank. The amount of the acid catalyst fed here is preferably from 1 to 1,000 ppm by weight, more preferably from 5 to 50 ppm by weight, in terms of the concentration based on the amount of raw material 1,4BG charged over time.

The reaction temperature that is the internal temperature of the liquid phase part inside the reaction tank is preferably from 80 to 250° C., more preferably from 100 to 200° C., still more preferably from 120 to 180° C. As this temperature is lower, productivity of THF tends to significantly decrease, whereas as this temperature is higher, increase in the trace byproduct or use of an expensive material in the case of using a strong acid is inevitably involved. Also, as the reaction temperature is higher, a larger amount of gamma butyrolactone tends to be contained in the condensate and since 1,4BG is also entrained to make the 1,4BG concentration high, the reflux ratio may be increased.

As for the reaction pressure, an arbitrary pressure may be employed, but the pressures is, in terms of absolute pressure, preferably from 10 to 1,000 kPa, more preferably from 100 to 500 kPa. If the pressure is too low, a large amount of gamma butyrolactone tends to be contained in the condensate and since 1,4BG is also entrained to make the 1,4BG concentration high, the reflux ratio may be increased. On the other hand, if the pressure is too high, a high reaction temperature is required and due to overheating of the reactor, the heat exchange efficiency decreases.

EXAMPLES

The present invention is described in greater detail below by referring to Examples, but the present invention is not limited to these Examples as long as the gist of the present invention is observed.

In the following Examples, the analysis of water was performed using a Karl-Fischer method. The analysis of each of tetrahydrofuran, gamma butyrolactone, 1,4BG and a dimer of 1,4-butanediol and gamma butyrolactone was performed by gas chromatography, and the concentration was calculated from the area percentage.

Incidentally, a value obtained by subtracting the water concentration from 100 wt % was calculated, and with respect to the value obtained, the percentage (wt %) of remaining component was calculated from the area percentage of each component in the gas chromatography.

Example 1

A glass-made 500-mL flask provided with a glass-made cooling tube for distillation, a raw material inlet tube and a nitrogen inlet tube was charged with 200 g of 1,4-butanediol containing 0.18 wt % of gamma butyrolactone and 0.4 g (0.2 wt %) of para-toluenesulfonic acid, and the contents were heated to an internal temperature of 145° C. by using an oil bath. Nitrogen was introduced at 300 mL/min into the reaction solution and after the internal liquid temperature settled at 145° C., the obtained condensate was withdrawn out as a product liquid to a glass-made storage tank. A tetrahydrofuran-containing condensate discharged as a product gas from the gas phase part of the flask and condensed in a condenser was obtained at 49 g/hr. At this time, the temperature of the liquid condensation region was 73.0° C., and the reflux ratio was 0.1. Also, the amount of liquid phase was adjusted to become 200 mL and thereafter, 1,4-butanediol containing 0.18 wt % of gamma butyrolactone was continuously fed at 52 g/hr so as to keep the amount of liquid phase constant. At this feeding, para-toluenesulfonic acid dissolved in a 1,4-butanediol solution to make an amount of 0.48 mg/hr (concentration of para-toluenesulfonic acid in 1,4BG: 12 ppm by weight) was continuously added together. The average residence time of raw material 1,4-butanediol for the volume of the liquid phase part was 4 hr. The reaction by heating, the distillation out of product from the gas phase part, and the feeding of raw material were continued for 5 hr. The amount of the condensate obtained was 281 g, and the composition thereof was composed of 76.2 wt % of tetrahydrofuran, 20.9 wt % of water and 1,525 ppm by weight of gamma butyrolactone. The ratio of gamma butyrolactone distilled out to gamma butyrolactone fed was 85%. Heating was stopped after passing 5 hours from the initiation of operation, and the liquid in the flask reactor was collected. During the collection, discharge of the liquid in the flask was not performed. The collected liquid in the flask reactor amounted to 164 g and as a result of analysis of the collected liquid, it was found that 1,722 ppm by weight of gamma butyrolactone was contained, and the selectivity of tetrahydrofuran was 99.5%. The dimer of 1,4-butanediol and gamma butyrolactone, which gives an indication of a high-boiling component, amounted to 0.08 wt %. The ratio of the dimer production to the THF production was 0.06%.

Example 2

The production was performed entirely in the same manner as in Example 1 except for changing the internal liquid temperature to 155° C. A tetrahydrofuran-containing condensate discharged as a product gas from the gas phase part of the flask and condensed in a condenser was obtained at 67 g/hr. At this time, the temperature of the liquid condensation region was 82.0° C., and the reflux ratio was 0.1. The 1,4-butanediol containing 0.18 wt % of gamma butyrolactone and 12 ppm by weight of para-toluenesulfonic acid was continuously fed at 65 g/hr. The average residence time of raw material 1,4-butanediol for the volume of the liquid phase part was 3 hr. The reaction by heating, the distillation out of product from the gas phase part, and the feeding of raw material were continued for 3.8 hr. The amount of the condensate obtained was 287 g, and the composition thereof was composed of 76.5 wt % of tetrahydrofuran, 21.1 wt % of water and 1,496 ppm by weight of gamma butyrolactone. The ratio of gamma butyrolactone distilled out to gamma butyrolactone fed was 85%. Heating was stopped after passing 3.8 hours from the initiation of operation, and the liquid in the flask reactor was collected. During the collection, discharge of the liquid in the flask was not performed. The collected liquid in the flask reactor amounted to 160 g and as a result of analysis of the collected liquid, it was found that 1,646 ppm by weight of gamma butyrolactone was contained, and the selectivity of tetrahydrofuran was 99.4%. The dimer of 1,4-butanediol and gamma butyrolactone, which gives an indication of a high-boiling component, amounted to 0.04 wt %. The ratio of the dimer production to the THF production was 0.03%.

Example 3

The production was performed entirely in the same manner as in Example 1 except that the amount of nitrogen introduced into the reaction solution was changed to 200 mL/min. A tetrahydrofuran-containing condensate discharged as a product gas from the gas phase part of the flask and condensed in a condenser was obtained at 47 g/hr. At this time, the temperature of the liquid condensation region was 73.0° C., and the reflux ratio was 0.1. The 1,4-butanediol containing 0.18 wt % of gamma butyrolactone and 12 ppm by weight of para-toluenesulfonic acid was continuously fed at 49 g/hr. The average residence time of raw material 1,4-butanediol for the volume of the liquid phase part was 4 hr. The reaction by heating, the distillation out of product from the gas phase part, and the feeding of raw material were continued for 5.2 hr. The amount of the condensate obtained was 281 g, and the composition thereof was composed of 78.0 wt % of tetrahydrofuran, 20.8 wt % of water and 1,470 ppm by weight of gamma butyrolactone. The ratio of gamma butyrolactone distilled out to gamma butyrolactone fed was 81%. Heating was stopped after passing 5.2 hours from the initiation of operation, and the liquid in the flask reactor was collected. During the collection, discharge of the liquid in the flask was not performed. The collected liquid in the flask reactor amounted to 163 g and as a result of analysis of the collected liquid, it was found that 2,561 ppm by weight of gamma butyrolactone was contained, and the selectivity of tetrahydrofuran was 99.9%. The dimer of 1,4-butanediol and gamma butyrolactone, which gives indication of a high-boiling component, amounted to 0.10 wt %. The ratio of the dimer production to the THF production was 0.07%.

Example 4

The production was performed entirely in the same manner as in Example 1 except that the amount of nitrogen introduced into the reaction solution was changed to 150 mL/min. A tetrahydrofuran-containing condensate discharged as a product gas from the gas phase part of the flask and condensed in a condenser was obtained at 43 g/hr. At this time, the temperature of the liquid condensation region was 76.0° C., and the reflux ratio was 0.1. The 1,4-butanediol containing 0.18 wt % of gamma butyrolactone and 12 ppm by weight of para-toluenesulfonic acid was continuously fed at 34 g/hr. The average residence time of raw material 1,4-butanediol for the volume of the liquid phase part was 5.9 hr. The reaction by heating, the distillation out of product from the gas phase part, and the feeding of raw material were continued for 5.9 hr. The amount of the condensate obtained was 248 g, and the composition thereof was composed of 79.6 wt % of tetrahydrofuran, 21.6 wt % of water and 813 ppm by weight of gamma butyrolactone. The ratio of gamma butyrolactone distilled out to gamma butyrolactone fed was 40%. Heating was stopped after passing 5.9 hours from the initiation of operation, and the liquid in the flask reactor was collected. During the collection, discharge of the liquid in the flask was not performed. The collected liquid in the flask reactor amounted to 181 g and as a result of analysis of the collected liquid, it was found that 2,463 ppm by weight of gamma butyrolactone was contained, and the selectivity of tetrahydrofuran was 99.0%. The dimer of 1,4-butanediol and gamma butyrolactone, which is indicative of a high-boiling component, amounted to 0.11 wt %. The ratio of the dimer production to the THF production was 0.10%.

Example 5

The production was performed entirely in the same manner as in Example 1 except that the amount of nitrogen introduced into the reaction solution was changed to 75 mL/min. A tetrahydrofuran-containing condensate discharged as a product gas from the gas phase part of the flask and condensed in a condenser was obtained at 36 g/hr. At this time, the temperature of the liquid condensation region was 80.0° C., and the reflux ratio was 0.1. The 1,4-butanediol containing 0.18 wt % of gamma butyrolactone and 12 ppm by weight of para-toluenesulfonic acid was continuously fed at 44 g/hr. The average residence time of raw material 1,4-butanediol for the volume of the liquid phase part was 4.5 hr. The reaction by heating, the distillation out of product from the gas phase part, and the feeding of raw material were continued for 5.7 hr. The amount of the condensate obtained was 233 g, and the composition thereof was composed of 77.0 wt % of tetrahydrofuran, 20.4 wt % of water and 538 ppm by weight of gamma butyrolactone. The ratio of gamma butyrolactone distilled out to gamma butyrolactone fed was 24%. Heating was stopped after passing 5.7 hours from the initiation of operation, and the liquid in the flask reactor was collected. During the collection, discharge of the liquid in the flask was not performed. The collected liquid in the flask reactor amounted to 220 g and as a result of analysis of the collected liquid, it was found that 2,275 ppm by weight of gamma butyrolactone was contained, and the selectivity of tetrahydrofuran was 99.2%. The dimer of 1,4-butanediol and gamma butyrolactone, which gives an indication of a high-boiling component, amounted to 0.11 wt %. The ratio of the dimer production to the THF production was 0.12%.

Comparative Example 1

The production was performed entirely in the same manner as in Example 1 except that the amount of nitrogen introduced into the reaction solution was changed to 5 mL/min. A tetrahydrofuran-containing condensate discharged as a product gas from the gas phase part of the flask and condensed in a condenser was obtained at 34 g/hr. At this time, the temperature of the liquid condensation region was 78.0° C., and the reflux ratio was 0.1. The 1,4-butanediol containing 0.18 wt % of gamma butyrolactone and 12 ppm by weight of para-toluenesulfonic acid was continuously fed at 44 g/hr. The average residence time of raw material 1,4-butanediol for the volume of the liquid phase part was 4.5 hr. The reaction by heating, the distillation out of product from the gas phase part, and the feeding of raw material were continued for 6 hr. The amount of the condensate obtained was 217 g, and the composition thereof was composed of 82.7 wt % of tetrahydrofuran, 18.3 wt % of water and 373 ppm by weight of gamma butyrolactone. The ratio of gamma butyrolactone distilled out to gamma butyrolactone fed was 18%. Heating was stopped after passing 6.0 hours from the initiation of operation, and the liquid in the flask reactor was collected. During the collection, discharge of the liquid in the flask was not performed. The collected liquid in the flask reactor amounted to 229 g and as a result of analysis of the collected liquid, it was found that 1,960 ppm by weight of gamma butyrolactone was contained, and the selectivity of tetrahydrofuran was 99.6%. The dimer of 1,4-butanediol and gamma butyrolactone, which gives an indication of a high-boiling component, amounted to 0.14 wt %. The ratio of the dimer production to the THF production was 0.17%.

While the invention has been described in detail and with reference to specific embodiments thereof, it will be apparent to one skilled in the art that various changes and modifications can be made therein without departing from the spirit and scope thereof. This application is based on a Japanese patent application filed on Jul. 4, 2011 (Application No. 2011-148329), the content thereof being incorporated herein by reference.

The invention claimed is:

1. A method for producing tetrahydrofuran, comprising:
    feeding raw material 1,4-butanediol comprising gamma butyrolactone to a reaction tank;
    performing a dehydration cyclization reaction to produce tetrahydrofuran in the presence of a homogeneous acid catalyst having a pKa of 4 or less and dissolvable in 1,4-butanediol;
    introducing a gas comprising tetrahydrofuran, gamma butyrolactone, and water in the reaction tank into a heat exchanger; and
    obtaining a condensate from an outlet of the heat exchanger,
    wherein a ratio of a concentration of gamma butyrolactone in the condensate with respect to a concentration of gamma butyrolactone in the raw material 1,4-butanediol is from 20 to 100%.

2. The method according to claim 1, wherein a temperature of a liquid phase in the reaction tank is from 80 to 250° C.

3. The method according to claim 1, wherein a concentration of the homogeneous acid catalyst in the reaction tank is from 0.01 to 20.0 wt %.

4. The method according to claim 1, wherein the homogeneous acid catalyst is mixed with and dissolved in the raw material 1,4-butanediol and then fed to the reaction tank.

5. The method according to claim 1, wherein a concentration of gamma butyrolactone in the reaction tank is maintained at from 20 ppm by weight to 1 wt %.

\* \* \* \* \*